US008841516B2

(12) United States Patent
de Milliano et al.

(10) Patent No.: US 8,841,516 B2
(45) Date of Patent: Sep. 23, 2014

(54) *FUSARIUM* RESISTANT CUCUMBER PLANTS

(75) Inventors: Maarten Johan Kulilela de Milliano, Rotterdam (NL); Roelof Tjallo Folkertsma, Den Haag (NL); Martinus Quirinus Maria van Paassen, Medemblik (NL); Jeroen Sebastiaan de Vries, Den Haag (NL); Marianne Beatrix Sela, Rotterdam (NL)

(73) Assignee: Monsanto Invest B.V., Bergschenhoek (NL)

( * ) Notice: Subject to any disclaimer, the term of this patent is extended or adjusted under 35 U.S.C. 154(b) by 165 days.

(21) Appl. No.: 13/203,269

(22) PCT Filed: Mar. 1, 2010

(86) PCT No.: PCT/NL2010/050101
§ 371 (c)(1),
(2), (4) Date: Nov. 7, 2011

(87) PCT Pub. No.: WO2010/098670
PCT Pub. Date: Sep. 2, 2010

(65) Prior Publication Data
US 2012/0066790 A1 Mar. 15, 2012

(30) Foreign Application Priority Data
Feb. 27, 2009 (EP) ..................................... 09153969

(51) Int. Cl.
*A01H 5/10* (2006.01)
*A01H 5/00* (2006.01)
*A01H 4/00* (2006.01)
*C12N 15/82* (2006.01)

(52) U.S. Cl.
CPC .................................. *C12N 15/8282* (2013.01)
USPC ........... 800/307; 800/260; 800/265; 800/266; 800/267

(58) Field of Classification Search
None
See application file for complete search history.

(56) References Cited

FOREIGN PATENT DOCUMENTS

EP    1782685 A1    5/2007

OTHER PUBLICATIONS de Ruiter, et al., "Combining QTLs for Resistance to CYSDV and Powdery Mildew in a Single Cucumber Line," Cucurbitaceae 2008, Proceedings of the IXth EUCARPIA Meeting on Genetics and Breeding of Cucurbitaceae.
Fazio, et al., "Genetic Mapping and QTL Analysis of Horticultural Traits in Cucumber (*Cucumis sativus* L.) Using Recombinant Inbred Lines," Theor Appl Genet (2003) 107:864-874.
Guan, et al., "Construction of a BAC Library From Cucumber (*Cucumis sativus* L.) and Identification of Linkage Group Specific Clones," Natural Science, 18 (2008) 143-147.
Mao, et al., "Analysis on the Inheritance of Resistance to *Fusarium* Wilt Race 4 and Cucumber Scab and Their Linkage in WIUS2757," Scientia Agricultura Sinica, 208, 41(10): 3382-3388.
Park, et al., "A Genetic Map of Cucumber Composed of RAPDs RFLPs, AFLPs and Loci Conditioning Resistance to Papaya Ringspot and Zucchini Yellow Mosaic Viruses," Genome, 43: 1003-1010 (2000).
Sakata, et al., "QTL Analysis of Powdery Mildew Resistance in Cucumber (*Cucumis sativus* L.)," Theor Appl Genet, (2006) 112: 243-250.
Schrader, et al., "Cucumber Production in California," University of California, Agriculture and Natural Resources.
Staub, et al., "Cucumber Inbred Line USDA 6632E," USDA-ARS Vegetable Crops Research Unit, University of Wisconsin-Madison Department of Horticulture, Jun. 2001.
Vakalounakis, J., "Inheritance and Genetic Linkage of *Fusarium* Wilt (*Fusarium Oxysporum* f.sp. cucumerinum Race 1) and Scab (*Cladosporium cucumerinum*) Resistance Genes in Cucumber (*Cucumis sativus*)," Ann. Appl. Biol. (1993), 123, 359-365.
Vakalounakis, J., "Allelism of the F cu-1 and Foc Genes Conferring Resistance to *Fusarium* Wilt in Cucumber," European Journal of Plant Pathology, 102: 855-858, 1996.
Zhou, et al., "Molecular Analysis of Introgression Lines From Cucumis Hystrix Chakr. To *C. sativus* L.," Scientia Horticulturae, 119 (2009) 232-235.

*Primary Examiner* — Brent T Page
(74) *Attorney, Agent, or Firm* — Dentons US LLP

(57) ABSTRACT

The present invention relates to a plant of a cucumber breeding line comprising an introgression from cucumber inbred line URS 189, a representative sample of seed of which has been deposited with the NCIMB, Aberdeen, Scotland under accession number NCIMB 41612 and depositors reference URS 189, or a *Fusarium*-resistant offspring plant of line URS 189, wherein said introgression confers to said plant of said cucumber breeding line resistance to the causal agent of *Fusarium* stem and root rot *Fusarium oxysporum* f. sp. *radicis cucumerinum* (Forc).

25 Claims, 2 Drawing Sheets

FUSARIUM RESISTANT CUCUMBER PLANTS

RELATED APPLICATION DATA

This application is a National Stage Application under 35 U.S.C. 371 of co-pending PCT application PCT/NL2010/050101 designating the United States and filed Mar. 1, 2010; which claims the benefit of EP patent application number 09153969.2 and filed Feb. 27, 2009each of which are hereby incorporated by reference in their entireties.

FIELD OF THE INVENTION

The present invention relates to plant breeding, more in particular, the present invention relates to *Fusarium* resistant cucumber plants and to methods for producing *Fusarium* resistant cucumber plants. The invention further relates to cucumber plants obtained by the method of the present invention and to seeds from *Fusarium* resistant cucumber plants.

BACKGROUND OF THE INVENTION

Cucumber (*Cucumis sativus*) is a major vegetable crop worldwide and among the most important crop species in the Cucurbitaceae family. They are eaten as a vegetable, either fresh, cooked, or made into pickled cucumbers. The more than 100 varieties produce oblong fruits ranging in size from small pickling to long Dutch cucumbers and from can range in color from white, yellow or brown, to a dark green for the cultivated varieties. Cucumbers are generally considered less nutritious than most other vegetables, the fresh cucumber is a good source of vitamins A, B1, B5, B6, B9, C, and K, and minerals. Most greenhouse varieties produce fruit without pollination and are gynoecious with respect to flowering, (i.e. produce predominantly female flowers).

*Fusarium* stem and root rot of greenhouse cucumber is predominantly caused by *Fusarium oxysporum* f. sp. *radicis cucumerinum* (Forc). An additional causal agent of *Fusarium* stem and root rot is *Fusarium oxysporum* f. sp. *cucumerinum* (Foc). Chemical control of infection by *Fusarium* is performed by substances such as formaline. It is generally understood that formaline will be banned as pesticide.

WO02062130 describes methods for the production of cucumber plants that are genetically resistant to *Fusarium oxysporum* f. sp. *radicis-cucumerinum* (Forc). The method essentially comprises crossing a Forc-resistant cucumber plant designated C566 with a cucumber plant displaying desirable phenotypic characteristics, or using a plant of designation C566 as a rootstock. Using this accession as a resistance source in breeding in the absence of molecular tools such as markers imposes an undue burden to the breeding program and is virtually unfeasible. Crosses of C566 with susceptible lines resulted in nearly susceptible F1 hybrids. The BC1 generation with the elite parent was completely susceptible. These observations are indicative of a recessive mode of inheritance and poor heritability of resistance to *Fusarium* derived from C566. In addition, it is not known whether plants of designation C566 exhibit resistance to *Fusarium oxysporum* f. sp. *cucumerinum* (Foc). These attributes strongly reduce the attractiveness of C566 as a source for resistance to *Fusarium* in cucumber breeding programs. Hence, there is a need for plants that can serve as source for commercial cucumber varieties that can provide resistance to both Forc and Foc. In addition, it is preferred that such plants can be used to produce progeny plants that exhibit a high level of resistance at high frequency, and that elite inbred lines can be produced as parents for producing commercial seed lots that provide resistant progeny with high reproducibility.

SUMMARY OF THE INVENTION

The present inventors have now discovered additional sources for resistance to Forc and Foc. It was found that these sources could be used to produce inbred lines that produce offspring with high heritability of the *Fusarium*-resistance.

Based on this finding, the inventors provide a novel genetic basis for the desirable phenotypic characteristic of *Fusarium*-resistance. This genetic basis is present in the two cucumber lines indicated herein as URS 189 and MC1278. URS 189 is fully resistant to Forc and Foc. MC1278 harbours intermediate resistance to Forc. The genetic basis for *Fusarium*-resistance of MC1278 is incorporated into a recombinant inbred line, which is provided in the present invention as a seed deposit. In a first aspect, the present invention provides a plant of a cucumber breeding line comprising an introgression from cucumber inbred line URS 189, a representative sample of seed of which has been deposited with the NCIMB, Aberdeen, Scotland under accession number NCIMB 41612 and depositors reference URS 189, or a *Fusarium*-resistant offspring plant of line URS 189, wherein said introgression confers to said plant of said cucumber breeding line resistance to the causal agent of *Fusarium* stem and root rot *Fusarium oxysporum* f. sp. *radicis cucumerinum* (Forc). The plant of the invention exhibits high heritability of the resistance trait. Typically, more than 40% of the F1 offspring plants, preferably more than 42%, 43%, 44%, 45%, or 46% of the F1 offspring plants is resistant to *Fusarium*.

The introgression from cucumber inbred line URS 189 provided to said plant of a cucumber breeding line contains the QTL from inbred line URS 189 as identified herein, or a portion of that QTL that confers to said plant resistance to the causal agent of *Fusarium* stem and root rot *Fusarium oxysporum* f. sp. *radicis cucumerinum* (Forc).

The QTL as referred to in embodiments of the present invention may be any of the QTLs as referred to in Table 6. Said QTL is indicated by either one or a combination of markers as listed in Tables 6 and 7. Preferably, said QTL is indicated by either one or a combination of markers for linkage group N as listed in Table 6. A highly preferred marker is SEQ ID NO:5. The term "is indicated" refers to the fact that the marker is linked to the QTL and can therefore be used to monitor successful introgression of the QTL, or the resistance-conferring part thereof, from a source plant into a recipient plant (e.g. from a parent into an offspring) by screening the nucleic acid of said recipient plant (for instance the breeding line of the present invention) for the presence of one or more of said markers to thereby provide an estimate of the chance that the recipient plant contains the QTL, or said resistance conferring part thereof.

In a preferred embodiment, the plant of the invention contains at least one allele that confers said resistance to *Fusarium*. As the trait conferred by the introgression was found to be additive, rather than dominant or recessive, the plant of the invention s preferably homozygous.

The QTL of the invention is preferably not genetically linked to Ccu, a locus conferring resistance to *Cladosporium cucumerinum*.

In a further preferred embodiment of this aspect, said *Fusarium*-resistant offspring plant is recombinant inbred line (RIL) 05 UR 0327, a representative sample of seed of which has been deposited with the NCIMB, Aberdeen, Scotland under accession number NCIMB 41611 and depositors reference 05 UR 0327.

In yet another preferred embodiment of this aspect, said plant comprises at least two introgressions from recombinant inbred line (RIL) 05 UR 0327, wherein both of said two introgressions confer resistance to the causal agent of *Fusarium* stem and root rot *Fusarium oxysporum* f. sp. *radicis cucumerinum* (Forc), and wherein said at least two introgressions are located on separate linkage groups.

In another preferred embodiment, said plant is a plant of an essentially homozygous pure elite breeding line.

In yet another preferred embodiment of this aspect, said plant is resistant to the causal agent of *Fusarium* stem and root rot *Fusarium oxysporum* f. sp. *cucumerinum* (Foc), and to *Fusarium solani* f. sp *cucurbitae* (Fsc).

In another aspect, the present invention provides a cucumber seed produced by crossing or selfing the cucumber plant of the present invention as described above.

In another aspect, the present invention provides a cucumber plant produced by growing the seed of the present invention. Preferably, said plant is resistant to Forc, preferably to Forc, Foc and Fsc.

In another aspect, the present invention provides a plant part of the plant of the present invention. Preferably the plant part is a (part derived from) a cucumber fruit or seed.

In another aspect, the present invention provides a method for producing a hybrid cucumber seed comprising crossing the plant according to the present invention as described above with another cucumber plant and harvesting the resultant hybrid cucumber seed. In a preferred embodiment of this aspect, said other cucumber plant is plant of a breeding line of cucumber, more preferably a plant according to the present invention of a different elite line.

In another aspect, the present invention provides a hybrid cucumber seed produced by the method of the present invention.

In another aspect, the present invention provides a hybrid cucumber plant, produced by growing the hybrid cucumber seed according to the present invention. Preferably, said hybrid cucumber plant is resistant to Forc, preferably to Forc, Foc and Fsc.

In another aspect, the present invention provides a plant part of the hybrid cucumber plant according to the present invention.

In another aspect, the present invention provides a method for improving the *Fusarium*-resistance of a plant of a cucumber breeding line comprising introgressing into said plant a genomic segment from cucumber accession URS 189, a representative sample of seed of which has been deposited with the NCIMB, Aberdeen, Scotland under accession number NCIMB 41612 and depositors reference URS 189, or a *Fusarium*-resistant offspring plant of line URS 189, conferring resistance to *Fusarium*, said method comprising the steps of:

a) crossing a plant of a cucumber breeding line with a plant of cucumber line URS 189 or a *Fusarium*-resistant offspring plant thereof;

b) selecting a progeny cucumber plant resulting from said crossing having an introgression from cucumber accession URS 189 or from said *Fusarium*-resistant offspring plant of line URS 189 conferring resistance to *Fusarium*;

c) selfing said progeny cucumber plant selected in step (b) and/or backcrossing said progeny cucumber plant selected in step (b) using said cucumber breeding line as a recurrent parent;

d) selecting a progeny cucumber plant resulting from the selfing or backcrossing in step (c) having an introgression from cucumber accession URS 189 or from said *Fusarium*-resistant offspring plant of line URS 189, conferring resistance to *Fusarium*;

e) repeating said steps of selfing and/or backcrossing and selection of steps (c) and (d), to thereby provide a plant of a cucumber breeding line essentially homozygous for said introgression, wherein preferably at least one selection as performed in steps (b) or (d) is performed by marker-assisted selection.

In a preferred embodiment of this aspect, said *Fusarium*-resistant offspring plant is recombinant inbred line (RIL) 05 UR 0327.

In a preferred embodiment of this aspect, said method comprises introgressing into said plant of said breeding line at least two introgressions from recombinant inbred line (RIL) 05 UR 0327, wherein both of said at least two introgressions confer resistance to the causal agent of *Fusarium oxysporum* f. sp. *radicis cucumerinum* (Forc), and wherein said at least two introgressions are located on separate linkage groups.

In another aspect, the present invention provides a method for improving the *Fusarium*-resistance of an F1 cucumber hybrid comprising introgressing into a first parental line of said F1 cucumber hybrid a genomic segment from cucumber accession URS 189, a representative sample of seed of which has been deposited with the NCIMB, Aberdeen, Scotland under accession number NCIMB 41612 and depositors reference URS 189, or a *Fusarium*-resistant offspring plant of line URS 189, conferring resistance to *Fusarium*, said method comprising the steps of:

a) crossing a plant of at least a first parental line of said F1 cucumber hybrid with a plant of cucumber line URS 189 or a *Fusarium*-resistant offspring plant of line URS 189;

b) selecting a progeny cucumber plant resulting from said crossing having an introgression from cucumber accession URS 189 or from said *Fusarium*-resistant offspring plant of line URS 189 conferring resistance to *Fusarium*;

c) selfing said progeny cucumber plant selected in step (b) and/or backcrossing said progeny cucumber plant using said first parental line of said F1 cucumber hybrid as a recurrent parent;

d) selecting a progeny cucumber plant resulting from the selfing or backcrossing in step (c) having an introgression from cucumber accession URS 189 or from said progeny plant of line URS 189 conferring resistance to *Fusarium*;

e) repeating said steps of selfing and/or backcrossing and selection of steps (c) and (d) to provide a first parental line of said F1 cucumber hybrid essentially homozygous for said introgression, f) using said first parental line obtained in step (e) as a parental line for the production of an F1 hybrid having resistance to *Fusarium*, wherein preferably at least one selection as performed in steps (b) or (d) is performed by marker-assisted selection.

In a preferred embodiment of this aspect, said method further comprises introgressing into said first parental line or in a second parental line of said F1 cucumber hybrid at least two introgressions from recombinant inbred line (RIL) 05 UR 0327, wherein both of said at least two introgressions confer resistance to the causal agent of *Fusarium oxysporum* f. sp. *radicis cucumerinum* (Forc), and wherein said introgressions are located on separate linkage groups.

In preferred embodiments of methods of the invention for improving the *Fusarium*-resistance of a plant of a cucumber breeding line or of an F1 cucumber hybrid, said marker-assisted selection procedure comprises the selection for markers having the sequence of any one of SEQ ID No: 1-5.

In another aspect, the present invention provides a *Fusarium*-resistant cucumber breeding line or a *Fusarium*-resistant F1 cucumber hybrid obtainable by a method according to the present invention.

In another aspect, the present invention provides an isolated nucleic acid sequence comprising a QTL associated with resistance to *Fusarium* in cucumber, wherein said QTL is defined by:

i) the segment on linkage group G and/or R (table 6) associated with any one of the markers having the sequence of SEQ ID NO: 1-4;

ii) the segment on linkage group N (table 6) associated with the marker having the sequence of SEQ ID NO: 5.

In another aspect, the present invention provides the use of a genetic marker selected from the group consisting of markers of SEQ ID Nos 1-5, for the detection of a QTL associated with resistance to *Fusarium* in cucumber plants.

In another aspect, the present invention provides a method for selecting a cucumber plant or part thereof, including a seed, comprising the steps of:

(a) providing a progeny cucumber plant or part thereof by crossing a plant of a cucumber breeding line with a plant of cucumber line URS 189 or a *Fusarium*-resistant offspring plant of line URS 189;

(b) testing said progeny cucumber plant or part thereof for the presence of an introgression segment from cucumber accession URS 189 or from a *Fusarium*-resistant offspring plant of line URS 189;

(c) selecting said progeny cucumber plant or part thereof based on the information derived from said test in step (b); and (d) optionally using said information for further breeding considerations.

DETAILED DESCRIPTION OF THE INVENTION

Definitions

Figure 1A:
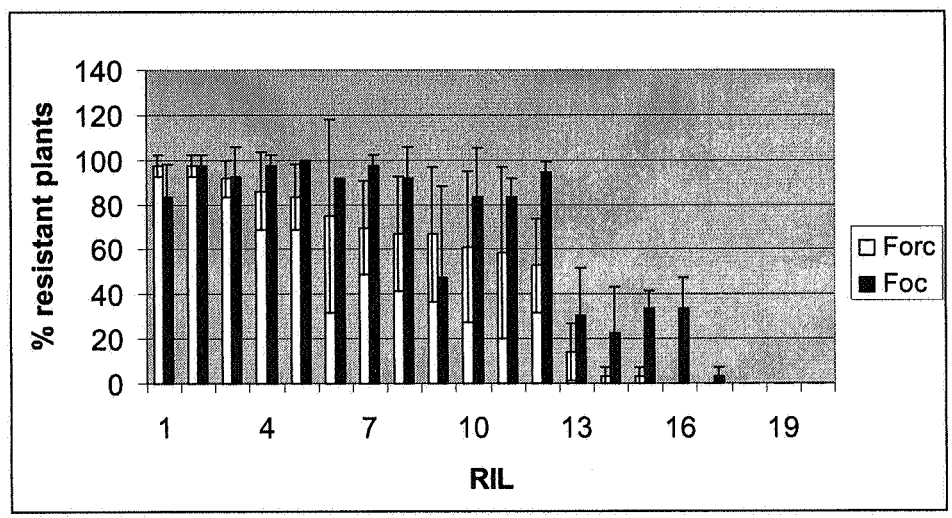
FIG. 1 indicates the tendency of resistance to Forc and Foc to co-segregate in a subset of RILs visualised by chart (1A) and scatter plot (1B).

The term "cucumber" as used herein refers to the species *Cucumis sativus* L., including *Cucumis sativus* L. var. *hardwickii* (Royle) or weedy cucumber, *Cucumis sativus* L. var. *sativus* or cultivated cucumber, *Cucumis sativus* L. var. *sativus* (Chinese Group) or netted yellow cucumber, *Cucumis sativus* L. (Gherkin Group) or pickling cucumber, *Cucumis sativus* L. var. *sativus* (Indian Group) or White-striped cucumber, *Cucumis sativus* L. var. *sativus* (Japanese Group) or Japanese cucumber, *Cucumis sativus* L. var. *sativus* (Lebanese Group) or Lebanese cucumber, *Cucumis sativus* L. var. *sativus* (Russian Group) or Russian cucumber, *Cucumis sativus* L. var. *sativus* (Seedless Group) or Seedless cucumber, *Cucumis sativus* L. var. *sativus* (Standard Group) or common cucumber/greenhouse cucumber, *Cucumis sativus* L. var. *sikkimensis* Hook. f. or brown netted cucumber, and *Cucumis sativus* L. var. *xishuangbannanesis* fined or Xishuangbanna gourd. Botanically speaking the name *Cucumis sativus* L. refers to the wild species but in the seed and vegetable trades it is used as a synonym for any longer botanical name that taxonomists may apply to the cultivated varieties. "*C. sativus* L. var. *sativus*" is generally used, based on the almost 1500 accessions entered in the USDA GRIN Database. However, this name may change in the future because taxonomists disapprove of domesticated plants referred to as botanical varieties "var.". The term "cucumber" includes reference to (American and European) pickling, (American and European) slicing, European greenhouse (parthenocarpic), middle-eastern (Beit Alpha types), and oriental trellis (Burpless) cucumbers.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). "Crossing" therefore generally refers to the fertilization of ovules of one individual with pollen from another individual, whereas "selfing" refers to the fertilization of ovules of an individual with pollen from the same individual. When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from said cell and their fusion in fertilization will result in an introgression event.

As used herein, the term "hybrid" means any offspring of a cross between two genetically unlike individuals, more preferably the term refers to the cross between two (elite) breeding lines which will not reproduce true to the parent from seed.

The term "breeding line", as used herein, refers to a line of a cultivated cucumber having commercially valuable or agronomically desirable characteristics, as opposed to wild varieties or landraces. In particular, the breeding line is characterized by having an excellent fruit quality (straight, cylindrical shape and uniform dark green color). The term includes reference to elite breeding line or elite line, which represents an essentially homozygous, e.g. inbred or doubled haploid, line of plants used to produce F1 hybrids. The term also includes reference to slicers, pickling, mini cucumbers, etc. A breeding line preferably has a yield above 0.5-1.5 kg of fruit per plant per week for an umbrella-trained crop. A cucumber breeding line preferably has a yield of at least 5, more preferably at least 6, or 7 kg per plant per growing period. The skilled person is familiar with methods to determine yield, for instance in order to determine the production in kg/plant, the fruits of a plant can be harvested 2 or 3 times a week during a period of at least 2 months wherein the plant produces fruits at harvest stage (fruits with a diameter of at least 4 cm in the middle of the fruit; fruits which stop growing for 3 days are also harvested, even if the diameter of 4 cm is not reached), and combining the weights determined at every harvest. A cucumber breeding line preferably comprises, in addition to *Fusarium* resistance, at least one additional resistance trait selected from powdery mildew and CYSDV.

As used herein, the term "*Fusarium*" refers to the causal agents of stem and root rot *Fusarium oxysporum* f. sp. *radi-*

*cis-cucumerinum* (Forc) and/or *Fusarium oxysporum* f. sp. *cucumerinum* (Foc), as well as to other *Fusarium* spp, such as *Fusarium solani* f. sp. *cucurbitae* (Fsc).

As used herein, the term "allele(s)" means any of one or more alternative forms of a gene or regulatory sequence, all of which alleles have at least one trait or characteristic in common, with a distinct effect on a phenotype. In a diploid cell or organism, the two copies of a given gene occupy corresponding loci on a pair of homologous chromosomes, which can be distinct alleles. Since the present invention relates to QTLs, i.e. genomic regions that may comprise one or more genes, but also regulatory sequences, it is in some instances more accurate to refer to "haplotype" (i.e. an allele of a chromosomal segment) in stead of "allele", however, in those instances, the term "allele" should be understood to comprise the term "haplotype".

A "gene" is defined herein as a hereditary unit (often indicated by a sequence of DNA) that occupies a specific location on a chromosome and that contains the genetic instruction for a potential phenotypic characteristics or trait in a plant. A QTL (quantitative trait locus) is a hereditary unit (typically delineated by one or more molecular genomic markers) that occupies a specific location on a chromosome and that contains the genetic instruction for (indirect) control of a particular phenotypic characteristics or trait in a plant. In contrast to a gene, which has a defined structure, a QTL is contained within a genetic interval. The size of the interval can be reduced without undue burden by persons skilled in the art by using fine mapping techniques well known in the art of genetic mapping and subsequent DNA sequencing routines. The QTL encodes at least one gene the expression of which, alone or in combination with other genes, results in the phenotypic trait being expressed, or encodes at least one regulatory region that controls the expression of at least one gene the expression of which, alone or in combination with other genes, results in the phenotypic trait being expressed. A QTL may be defined by indicating its genetic location in the genome of the donor of the introgression that contains the QTL using one or more molecular genomic markers. One or more markers, in turn, indicate a specific locus. Distances between loci on the same chromosome are measured by frequency of crossing-over between loci. The further apart two loci are, the more likely that a crossover will occur between them. Conversely, if two loci are close together, a crossover is less likely to occur between them. As a rule, one centimorgan (cM) is equal to 1% recombination between loci (markers). When a QTL can be delineated by multiple markers the genetic distance between the end-point markers is indicative of the size of the QTL. Markers that define the QTL may be markers that are linked to the QTL, i.e. markers that are in linkage disequilibrium with the QTL.

As used herein, the term "molecular genomic marker" or short "marker" is a polymorphic nucleic acid sequence, detected by various methods to visualize differences in characteristics of nucleic acid sequences. Examples of such methods are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. A "molecular marker linked to a QTL" as defined herein may thus refer to SNPs, insertion mutations as well as more usual AFLP markers or any other type of marker used in the field.

The term "associated with" as used herein with reference to the linkage between markers and phenotype refers to a distance of preferably less than 20 cM, preferably less than 10 cM, still more preferably less than 6, 5, 4, 3, 2, or 1 cM.

A "locus" is defined herein as the position that a given trait, QTL, gene, or marker occupies on a chromosome of a given plant species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "pure inbred" or "inbred" refers to a fully or predominantly homozygous plant or plant line obtained by repeated selfings.

A "recombination event" refers to a meiotic crossing-over event.

As used herein, the term "introgression" refers to a genomic segment that has moved from one species, variety, or cultivar into the genome of another species, variety or cultivar, by crossing those species, varieties or cultivars or by genetic modification (see below).

As used herein, the terms "introgressing", "introgress" and "introgressed" refer to both a natural and artificial process whereby individual genes or entire traits are moved from one species, variety or cultivar into the genome of another species, variety or cultivar, by crossing those species, varieties or cultivars. Common plant breeding practice usually involves selfing or backcrossing to the recurrent parent to provide for an increasingly homozygous plant having essentially the characteristics of the recurrent parent in addition to the introgressed gene or trait.

The term "backcross" refers to the process wherein the plant resulting from a cross between two parental lines is crossed with one of its parental lines. The parental line used in the backcross is referred to as the recurrent parent. Repeated backcrossing results in the genome becoming more and more homozygous or inbred and resembling more and more that of the recurrent parent.

The term "selfing" refers to the process of self-fertilization wherein an individual is pollinated or fertilized with its own pollen.

"Genetic engineering", "transformation" and "genetic modification" are all used herein as synonyms for the transfer of isolated and cloned genes or DNA fragments into the DNA, usually the chromosomal DNA or genome, of another organism.

As used herein, the term "plant part" indicates a part of the cucumber plant, including single cells and cell tissues such as plant cells that are intact in plants, cell clumps and tissue cultures from which cucumber plants can be regenerated.

Examples of plant parts include, but are not limited to, organelles, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation or pedigree.

As used herein, the term "variety" refers to a group of similar plants that by structural or genetic features and/or performance can be distinguished from other varieties within the same species.

The term "cultivar" (for cultivated variety) is used herein to denote a variety that is not normally found in nature but that has been created by humans, i.e. having a biological status other than a "wild" status, which "wild" status indicates the original non-cultivated, or natural state of a plant or accession. The term "cultivar" includes, but is not limited to, semi-natural, semi-wild, weedy, traditional cultivar, landrace, breeding material, research material, breeder's line, synthetic population, hybrid, founder stock/base population, inbred line (parent of hybrid cultivar), segregating population, mutant/genetic stock, and advanced/improved cultivar.

The term "elite background" is used herein to indicate that the genetic context or environment of a QTL or introgression has become that of a breeding line. In the present instance the natural background is the genetic background of Cucumber accession URS 189. A method that involves the transfer of DNA comprising the QTL from linkage group N (Table 6) or R/G of a plant of cucumber line URS 189 or 05 UR 0327 respectively to the same position on linkage group N or R and/or G of a plant of a breeding line will result in that QTL not being in its natural genetic background, but in an elite background. The term both includes heterozygous as well as homozygous situations.

DESCRIPTION OF THE PREFERRED EMBODIMENTS

Producing plants with resistance to Forc and Foc

Plant breeders and in particular seed companies employ elite breeding lines, generally referred to as "elite lines" to provide a constant quality product. The elite lines are the result of many years of inbreeding and combine multiple superior characteristics such as high yield, fruit quality, and resistance to pests, disease, or tolerance to abiotic stress. The average yield of these elite lines is generally much higher than the original wild (landrace) accessions from which many of the modern cucumbers are descendants. The elite lines can be used directly as crop plant, but are typically used to produce so-called F1 or single-cross hybrids, produced by a cross between two (homozygous or inbred) elite lines. The F1 hybrids thus combine the genetic properties of the two parents into a single plant. An add-on benefit of hybrids is that they express hybrid vigour or heterosis, the poorly understood phenomenon that hybrid plants grow better than either (inbred) parent and show higher yields.

Backcross or pedigree selection is one method by which breeders add desirable agronomic traits to their elite breeding lines. The method involves crossing the breeding line with a line that expresses the desirable trait followed by backcrossing offspring plants expressing the trait to the recurrent parent. As a result, the selection of an individual as a parent in a breeding program is based on the performance of its forebears. Such methods are most effective in breeding for qualitatively-inherited traits, i.e traits which are present or absent.

Recurrent selection is an alternative breeding method for improving breeding lines and involves systematic testing and selection of desirable progeny followed by recombination of the selected individuals to form a new population. Recurrent selection has proven effective for improving quantitative traits with low heritability, such as yield, in cucumber. Recurrent selection, however, decreases the rate of broadening genetic basis underlying the various traits in a breeding program, and its potential is therefore limited.

The present inventors discovered that in Cucumber accession URS 189, a gene or regulatory sequence associated with resistance to *Fusarium* is present on linkage group N (table 6). Linkage group N may be further characterized by (either) one or a combination of the well known markers for the respective linkage group as indicated in Table 6 in the Examples. The present inventors further discovered that in Cucumber accession MC1278, a gene or regulatory sequence associated with resistance to *Fusarium* is present on linkage group G and/or R (table 6). Linkage group N may be further characterized by (either) one or a combination of the well known markers for the respective linkage group as indicated in Table 6 in the Examples. This gene or regulatory sequence associated with the *Fusarium* resistance of Cucumber accession MC1278 was combined with the gene or regulatory sequence associated with the *Fusarium* resistance of accession URS 189 into RIL line 05 UR 0327.

A definitive chromosome number has not yet been assigned to the cucumber chromosomes on which the QTLs as defined herein are located. However, the chromosomes may be designated by reference to the linkage group (LG) on which these and other genomic regions are located. The term linkage group is used herein to refer to a physical genomic unit on which the resistance-conferring alleles are located, and which have the same hierarchical level as a chromosome.

A first method would comprise introgressing at least one QTL for resistance to Forc and Foc from a plant of Cucumber accession URS 189 or a *Fusarium*-resistant offspring plant thereof, into a plant of a cucumber line of interest. This will result in a situation wherein the QTL is in the genetic background of the cucumber line of interest. The establishment of the proper introgression in offspring plants may be monitored by using specific QTL-flanking markers.

Recombination is the exchange of information between two homologous chromosomes during meiosis. In a recombinant plant, DNA that is originally present on a specific location within the chromosome is exchanged for DNA from another plant (i.e. maternal for paternal or vice versa). In order to exchange only the required material, and maintain the valuable original information on the chromosome as much as possible, will usually require two crossover events. The normal way to find such a recombinant, is to screen a population of F2-plants. This population must be of sufficient size in order to detect the rare (low frequency) double recombinants. The frequency of recombination may be calculated as follows. For instance, a single recombinant in a 10 cM area can be found with a frequency of 10% (1 centimorgan is defined as 1% recombinant progeny in a testcross).

The present invention now provides for better models for marker assisted selection (MAS). The invention therefore relates to methods of plant breeding and to methods to select plants, in particular cucumber plants, particularly cultivated cucumber plants as breeder plants for use in breeding programs or cultivated cucumber plants for having desired genotypic or potential phenotypic properties, in particular related to producing quantities of valuable cucumber fruits, also referred herein to as agronomically desirable plants. Herein, a cultivated plant is defined as a plant being purposely selected or having been derived from a plant having been purposely selected in agricultural or horticultural practice for having desired genotypic or potential phenotypic properties, in particular a plant obtained by inbreeding.

Since the QTLs are additive (the hybrid between MC1278 or URS 189 or RIL and a susceptible inbred line is predominantly but not fully susceptible), the presence of QTLs in the offspring plants cannot be monitored in the F2 or BC1 by measuring the resistance of the plants. Resistant individuals among the progeny may harbour only one QTL, or may have escaped from infection. Hence, it is of particular advantage that the establishment of the proper introgression in offspring plants may be monitored by using the QTL-specific markers as provided herein, either in cis or in trans coupling as explained below. By using marker assisted selection (MAS) or marker assisted breeding (MAB) methods, the skilled person is therefore provided with methods for selecting plants carrying resistance loci and discarding plants lacking the potential of producing resistant progeny.

The present invention thus also provides methods for selecting a plant of the species *Cucumis sativus* exhibiting resistance to Forc and Foc comprising detecting in said plant the presence of one or two QTL as defined herein. In a preferred method of the invention for selecting such a plant the method comprises:

a) providing a sample of genomic DNA from a cucumber plant;

b) detecting in said sample of genomic DNA at least one molecular marker linked to the QTL.

The step of providing a sample of genomic DNA from a cucumber plant may be performed by standard DNA isolation methods well known in the art.

The step of detecting a molecular marker (step b) may, in a preferred embodiment, comprise the use of a set of complementary, bi-directional primers that were used in the AFLP method to produce the amplification product that represents the marker for the QTL. Such a set of primers is herein referred to as the primers that define the AFLP marker or marker-specific primers. Bi-directional means that the orientation of the primers is such that one functions as the forward and one as the reverse primer in an amplification reaction of nucleic acid.

Alternatively, the step of detecting a molecular marker (step b) may in another preferred embodiment, comprise the use of a nucleic acid probe having a base sequence which is substantially complementary to the nucleic acid sequence defining said molecular marker and which nucleic acid probe specifically hybridizes under stringent conditions with a nucleic acid sequence defining said molecular marker. A suitable nucleic acid probe may for instance be a single strand oligonucleotide of the amplification product corresponding to the marker.

The step of detecting a molecular marker (step b) may also comprise the performance of a unique nucleic acid amplification reaction on said genomic DNA to detect said QTL. This can suitable be done by performing a PCR reaction using a pair of marker-specific primers based on the internal or adjacent (up to 500 kilo base) sequence. In a preferred embodiment, said step b) comprises the use of at least one pair of primers defining an AFLP marker for said QTL, or a pair of primers which specifically hybridize under stringent conditions with the internal or adjacent nucleic acid sequence of an AFLP marker for said QTL.

The step of detecting an amplified DNA fragment having the predicted length or the predicted nucleic acid sequence of step d) is preferably performed such that the amplified DNA fragment has a length that corresponds (plus or minus a few bases, e.g. a length of one, two or three bases more or less) to the expected length as based on a similar reaction with the same primers with the DNA from the plant in which the marker was first detected or the nucleic acid sequence that corresponds (has a homology of more than 80%, preferably more than 90%, more preferably more than 95%, even more preferably more than 97%, still more preferably more than 99%) to the expected sequence as based on the sequence of the marker associated with that QTL in the plant in which said marker was first detected. The skilled person is aware that markers that are absent in plants having the introgression as defined herein (donor plans), while they are present in the plants receiving the introgression (recipient plants) (so-called trans-markers), may also be useful in assays for detecting the introgression among offspring plants, although detecting the presence of a specific introgression is not optimally demonstrated by the absence of a marker.

The step of detecting an amplified DNA fragment having the predicted length or the predicted nucleic acid sequence may be performed by standard gel-electrophoresis techniques, real time PCR, or by using DNA sequencers. The methods need not be described here as they are well known to the skilled person. It should be noted that the marker is defined based on its primer internal sequences in combination with the length of the amplification product and the position of the marker relative to other markers on a linkage map.

Molecular Markers and QTLs

Molecular markers are used for the visualisation of differences in nucleic acid sequences. This visualisation is possible due to DNA-DNA hybridisation techniques after digestion with a restriction enzyme (RFLP) and/or due to techniques using the polymerase chain reaction (e.g. STS, microsatellites, AFLP). All differences between two parental genotypes will segregate in a mapping population (e.g., BC1, F2) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a short genetic distance between markers on a chromosome. Comparing all recombination frequencies will result in the most logical order of the molecular markers on the chromosomes. This most logical order can be depicted in a linkage map. A group of adjacent or contiguous markers on the linkage map that is associated with resistance to *Fusarium*, pinpoints the position of a QTL associated with resistance to *Fusarium*.

The markers identified herein may be used in various aspects of the invention as will now be illustrated. Aspects of the invention are not limited to the use of the markers identified herein. It is stressed that the aspects may also make use of markers not explicitly disclosed herein or even yet to be identified. Other than the genetic unit "gene", on which the phenotypic expression depends on a large number of factors that cannot be predicted, the genetic unit "QTL" denotes a region on the genome that is directly related to a phenotypically quantifiable trait. Thus, while genes or their function per se bear little or no relation to plant breeding, a QTL is directly applicable to plant breeding.

The QTL from MC1278 (and 05 UR 0327) as identified herein is located on linkage group G and/or R (table 6) and the QTL from URS 189 as identified herein is located on linkage group N (table 6) and their location is best characterized by a number of otherwise arbitrary markers. In the present investigations amplified fragment length polymorphism (AFLP) markers, to detect single nucleotide polymorphisms (SNPs), and insertion deletions (INDELs), or microsatellite markers, although restriction fragment length polymorphism (RFLP) markers, sequence-characterized amplified region (SCAR) markers, cleaved amplified polymorphic sequence (CAPS) markers or isozyme markers or combinations of these markers might also have been used. In general, a QTL may span a region of several million bases. Therefore, providing the complete sequence information for the QTL is practically unfeasible but also unnecessary, as the way in which the QTL is first detected—through the observed correlation between the presence of a string of contiguous genomic markers and the presence of a particular phenotypic trait—allows one to trace amongst a population of offspring plants those plants that have the genetic potential for exhibiting a particular phenotypic trait. By providing a non-limiting list of markers, the present invention thus provides for the effective utility of the QTLs in a breeding program.

It is further important to note that the contiguous genomic markers can also be used to indicate the presence of the QTL (and thus of the phenotype) in an individual plant, i.e. they can be used in marker assisted selection (MAS) procedures. In principle, the number of potentially useful markers is limited but may be very large, and the skilled person may easily identify additional markers to those mentioned in the present application. Any marker that is linked to the QTL, e.g. falling within the physical boundaries of the genomic region spanned by the markers having established LOD scores above a certain threshold thereby indicating that no or very little recombination between the marker and the QTL occurs in crosses; as well as any marker in linkage disequilibrium to the QTL; as well as markers that represent the actual causal mutations within the QTL, may be used in MAS procedures.

This means that the markers identified herein, are mere examples of markers suitable for use in MAS procedures. Moreover, when the QTL, or the specific trait-conferring part thereof, is introgressed into another genetic background (i.e. into the genome of another plant line), then some markers may no longer be found in the offspring although the trait is present therein, indicating that such markers are outside the genomic region that represents the specific trait-conferring part of the QTL in the original parent line only and that the new genetic background has a different genomic organisation. Such markers of which the absence indicates the successful introduction of the genetic element in the offspring are called "trans markers" and may be equally suitable in MAS procedures under the present invention.

The pre-fixes P1 and P2 used herein in the marker annotations indicates the parent label (genomic background) of the marker, wherein P1 is URS 189 and P2 is the MC1278.

Upon the identification of the QTL, the QTL effect (the *Fusarium*-resistance) is confirmed by assessing the resistance of F4 QIRs or $BC_2S_1$ progenies respectively recombinant or segregating for the QTLs under investigation. Preferably, detecting the presence of a QTL of the invention is performed with at least one of the markers for a QTL as defined herein. The present invention therefore also relates to a method for detecting the presence of a QTL for *Fusarium*-resistance as defined herein in cucumber by the use of the said markers.

The nucleotide sequence of the QTLs of the present invention may be resolved by determining the nucleotide sequence of one or more markers associated with said QTL and designing internal primers for said marker sequences that may then be used to further determine the sequence the QTL adjacent to said marker sequences. For instance the nucleotide sequence of AFLP markers may be obtained by isolating said markers from the electrophoresis gel used in the determination of the presence of said markers in the genome of a subject plant, and determining the nucleotide sequence of said markers by for instance Sanger or pyro sequencing methods, well known in the art.

In embodiments of methods for detecting the presence of a QTL in a cucumber plant, the method may also comprise the steps of providing an oligonucleotide or polynucleotide capable of hybridizing under stringent hybridization conditions to a nucleic acid sequence of a marker linked to said QTL, contacting said oligonucleotide or polynucleotide with nucleic acid of a cucumber plant, and determining the presence of specific hybridization of said oligonucleotide or polynucleotide to said nucleic acid.

Preferably said method is performed on a nucleic acid sample obtained (isolated) from said cucumber plant, although in situ hybridization methods may also be employed. Alternatively, and in a more preferred embodiment, the skilled person may, once the nucleotide sequence of the QTL has been determined, design specific hybridization probes or oligonucleotides capable of hybridizing under stringent hybridization conditions to the nucleic acid sequence of said QTL and may use such hybridization probes in methods for detecting the presence of a QTL of the invention in a cucumber plant.

Production of Cucumber Plants Exhibiting *Fusarium*-Resistance by Transgenic Methods According to another aspect of the present invention, a nucleic acid (preferably DNA) sequence comprising one or more of the QTLs as defined herein may be used for the production of a cucumber plant exhibiting *Fusarium*-resistance. In this aspect, the invention provides for the use of QTLs as defined herein or *Fusarium*-resistance-conferring parts thereof, for producing a *Fusarium*-resistant cucumber plant as defined herein, which use involves the introduction of a nucleic acid sequence comprising said QTL in a suitable recipient plant. As stated, said nucleic acid sequence may be derived from a suitable donor plant. Suitable sources according to the present invention for the *Fusarium*-resistance QTLs are cucumber lines 05 UR 0327 and/or URS 189, preferably both sources are used additively as described herein. Representative samples of seed of cucumber lines 05 UR 0327 and URS 189 have been deposited with the NCIMB, Aberdeen, Scotland on 18 Feb. 2009 under depositors reference cucumber lines 05 UR 0327 and URS 189.

The nucleic acid sequence that comprises a QTL for *Fusarium*-resistance, or a *Fusarium*-resistance-conferring part thereof, may be transferred to a suitable recipient plant by any method available. For instance, the said nucleic acid sequence may be transferred by crossing a plant of line URS 189 with a selected breeding line which is susceptible to *Fusarium* or of which the resistance to *Fusarium* is to be improved, i.e. by introgression, by transformation, by protoplast fusion, by a doubled haploid technique or by embryo rescue or by any other nucleic acid transfer system, optionally followed by selection of offspring plants comprising the QTL (as assessed by markers) and/or exhibiting resistance to *Fusarium*. For transgenic methods of transfer a nucleic acid sequence comprising a QTL for resistance to *Fusarium* may be isolated from said donor plant by using methods known in the art and the thus isolated nucleic acid sequence may be transferred to the recipient plant by transgenic methods, for instance by means of a vector, in a gamete, or in any other suitable transfer element, such as a bombardment with a particle coated with said nucleic acid sequence.

Plant transformation generally involves the construction of a vector with an expression cassette that will function in plant cells. In the present invention, such a vector consists of a nucleic acid sequence that comprises a QTL for resistance to *Fusarium*, which vector may comprise a *Fusarium*-resistance gene that is under control of or operatively linked to a regulatory element, such as a promoter. The expression vector may contain one or more such operably linked gene/regulatory element combinations, provided that at least one of the genes contained in the combinations confers *Fusarium*-resistance. The vector(s) may be in the form of a plasmid, and can be used, alone or in combination with other plasmids, to provide transgenic plants that exhibit *Fusarium*-resistance, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (See e.g. Horsch et al., 1985. Science 227:1229-1231). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. Methods of introducing expression vectors into plant tissue include the direct infection or co-cultivation of plant cells with *Agrobacterium tumefaciens*. Descriptions of *Agrobacterium* vectors systems and methods for *Agrobacterium*-mediated gene transfer are provided in U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993 (Vectors for plant transformation. In: Glick B R and Thompson J E (Eds.) Methods in ant Molecular Biology & Biotechnology, CRC Press, pp. 89-119). General methods of culturing plant tissues are provided for example by Miki et al., 1993 (Procedures for Introducing Foreign DNA into Plants. In: Glick B R and Thompson J E (Eds.) Methods in Plant Molecular Biology & Biotechnology, CRC Press, pp. 67-88) and by Phillips, et al., 1988 (Cell/tissue culture and in vitro manipulation. In: G. F. Sprague & J. W. Dudley, eds. Corn and corn improvement, 3rd ed., p. 345-387. Madison, Wis., USA, American Society of Agronomy). A proper reference handbook for molecular cloning techniques and suitable expression vectors is Sambrook and Russell, 2001 (Molecular Cloning: A Laboratory Manual. New York, N.Y., USA., Cold Spring Harbor Laboratory Press).

Another method for introducing an expression vector into a plant is based on microprojectile-mediated transformation (particle bombardment) wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes. Another method for introducing DNA to plants is via the sonication of target cells. Alternatively, liposome or spheroplast fusion has been used to introduce expression vectors into plants. Direct uptake of DNA into protoplasts using $CaCl_2$ precipitation, polyvinyl alcohol or poly-L-ornithine has also been reported. Electroporation of protoplasts and whole cells and tissues has also been described.

Other well known techniques such as the use of BACs, wherein parts of the cucumber genome are introduced into bacterial artificial chromosomes (BACs), i.e. vectors used to clone DNA fragments (100- to 300-kb insert size; average, 150 kb) in *Escherichia coli* cells, based on naturally occurring F-factor plasmid found in the bacterium *E. coli* may for instance be employed in combination with the BIBAC system to produce transgenic plants.

Following transformation of cucumber target tissues, expression of the above described selectable marker genes allows for preferential selection of transformed cells, tissues and/or plants, using regeneration and selection methods now well known in the art.

Production of Cucumber Plants Exhibiting Resistance to *Fusarium* by Non-Transgenic Methods In an alternative embodiment for producing a cucumber plant exhibiting resistance to *Fusarium*, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a cucumber plant of accession URS 189. A second protoplast can be obtained from a second cucumber plant variety, preferably a cucumber line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising the QTL as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants.

The present invention also relates to a method for improving the *Fusarium*-resistance of a plant of a cucumber breeding line, comprising the steps of:

a) crossing a plant of a cucumber breeding line with a plant of cucumber line URS 189 or an offspring plant thereof harbouring the *Fusarium* resistance as described herein;

b) selecting a progeny cucumber plant resulting from said crossing having an introgression from cucumber accession URS 189 or an offspring plant thereof associated with resistance to *Fusarium*;

c) selfing and/or backcrossing said progeny cucumber plant selected in step (b) using said cucumber breeding line as a recurrent parent;

d) selecting a progeny cucumber plant resulting from the selfing or backcrossing in step (c) having an introgression from cucumber accession URS 189 or an offspring plant thereof associated with resistance to *Fusarium* e) repeating said steps of selfing and/or backcrossing and selection of steps (c) and (d) to provide a plant of a cucumber breeding line essentially homozygous for said introgression, wherein preferably at least one selection as performed in steps (b) or (d) is performed by marker-assisted selection.

In a preferred embodiment of such a method, said cucumber breeding line is an elite line.

In an alternative preferred embodiment of the above method, the marker-assisted selection procedure comprises the selection for at least one marker selected from the group consisting markers comprising a nucleotide sequence of SEQ ID NOs 1-5.

The introgression of the nucleic acid sequence comprising the QTL as described herein may suitably be accomplished by using traditional breeding techniques. The QTL is preferably introgressed into commercial cucumber varieties by using marker-assisted selection (MAS) or marker-assisted breeding (MAB). MAS and MAB involves the use of one or more of the molecular markers for the identification and selection of those offspring plants that contain one or more of the genes that encode for the desired trait. In the present instance, such identification and selection is based on selection of the QTL of the present invention or markers associated therewith. MAS can also be used to develop near-isogenic lines (NIL) harboring the QTL of interest, or the generation of QTL isogenic recombinants (QIRs), allowing a more detailed study of each QTL effect and is also an effective method for development of backcross inbred line (BIL) populations. Cucumber plants developed according to this embodiment can advantageously derive a majority of their traits from the recipient plant, and derive *Fusarium*-resistance from the donor plant.

Crossing can be achieved by mechanically pollinating the female flower of one parent plant with pollen obtained from male flowers of another parent plant. Elite cucumber lines may have strong female sex expression (many female flowers), but can still be used as pollen donors. Generally, cucumber seeds are sown from batches with at least 75% germination rate. Two weeks after sowing, lines that produce almost exclusively female flowers are induced for production of male flowers using silvernitrate, silverthiosulfate, or gibberellin by methods well known in the art. Generally male flowers occur in week 7.

As discussed briefly above, traditional breeding techniques can be used to introgress a nucleic acid sequence encoding for *Fusarium*-resistance into a recipient cucumber plant requiring *Fusarium*-resistance. In one method, which is referred to as pedigree breeding, a donor cucumber plant that exhibits *Fusarium*-resistance and comprising a nucleic acid sequence encoding for the QTL associated with *Fusarium*-resistance as defined herein is crossed with a recipient cucumber plant (preferably a plant of an elite line) that exhibits agronomically desirable characteristics, such as, but not limited to, disease resistance, insect resistance, valuable fruit characteristics, etc., but which is susceptible to *Fusarium*, or which requires improvement of *Fusarium*-resistance. The resulting plant population (representing the $F_1$ hybrids) is then self-pollinated and set seeds (F2 seeds). The F2 plants grown from the F2 seeds are then screened for *Fusarium*-resistance. The population can be screened in a number of different ways.

First, the population can be screened using a traditional resistance assays. Such assays are described herein. Second, marker-assisted selection can be performed using one or more of the hereinbefore-described molecular markers to identify those progeny that comprise a nucleic acid sequence encoding for *Fusarium*-resistance as defined herein. Other methods, described above by methods for detecting the presence of a QTL may be used. Also, marker-assisted selection can be used to confirm the results obtained from the *Fusarium*-resistance assays, and therefore, several methods may also be used in combination.

Inbred cucumber plant lines exhibiting resistance to *Fusarium* can be developed using the techniques of recurrent selection and backcrossing, selfing and/or dihaploids or any other technique used to make parental lines. In a method of recurrent selection and backcrossing, the *Fusarium*-resistance-conferring genetic element as disclosed herein can be introgressed into a target recipient plant (the recurrent parent) by crossing the recurrent parent with a first donor plant, which differs from the recurrent parent and is referred to herein as the "non-recurrent parent". The recurrent parent is a plant of which the *Fusarium*-resistance is to be improved and possesses agronomically desirable characteristics, such as, but not limited to disease resistance, insect resistance, valuable fruit characteristics, etc. The non-recurrent, or donor, parent is a plant of line URS 189 and/or a RIL line obtained from a cross between MC1278 and URS 189 as described herein (05 UR 0327) and comprises a nucleic acid sequence that encodes for *Fusarium*-resistance. Alternatively, the donor parent can be any plant variety or inbred line that is cross-fertile with the recurrent parent and has acquired the QTL for *Fusarium*-resistance in an earlier cross with a plant of line URS 189 and/or 05 UR 0327. The progeny resulting from a cross between the recurrent parent and non-recurrent parent is backcrossed to the recurrent parent. The resulting plant population is then screened for the desired characteristics, which screening may occur in a number of different ways. For instance, the population can be screened using phenotypic screens as described herein. As an alternative to phenotypic assays, marker-assisted selection (MAS) can be performed using one or more of the hereinbefore described molecular markers, hybridization probes or polynucleotides to identify progeny that comprise a nucleic acid sequence encoding *Fusarium*-resistance.

Following screening, the F1 hybrid plants that exhibit a *Fusarium*-resistant phenotype or, more preferably, genotype and thus comprise the requisite nucleic acid sequence encoding for resistance to *Fusarium* are then selected and backcrossed to the recurrent parent for a number of generations in order to allow for the cucumber plant to become increasingly elite. This process can be performed for two to five or more generations. In principle the progeny resulting from the process of crossing the recurrent parent with the non-recurrent parent are heterozygous for one or more genes that encode for *Fusarium*-resistance.

In general, a method of introducing a desired trait into a hybrid cucumber variety comprises the steps of:

(a) crossing an inbred cucumber parent with another cucumber plant that comprises one or more desired traits, to produce F1 progeny plants, wherein the desired trait is *Fusarium*-resistance as conferred by the QTL from URS 189, or an offspring plant thereof such as the RIL-line 05 UR 0327 as described herein;

(b) selecting said F1 progeny plants that have the desired trait to produce selected F1 progeny plants, preferably using molecular markers as defined herein;

(c) backcrossing the selected progeny plants with said inbred cucumber parent plant to produce backcross progeny plants;

(d) selecting for backcross progeny plants that have the desired trait and morphological and physiological characteristics of said inbred cucumber parent plant, wherein said selection comprises the isolation of genomic DNA and testing said DNA for the presence of at least one molecular marker for the QTL as defined above;

(e) repeating steps (c) and (d) two or more times in succession to produce selected third or higher backcross progeny plants;

(f) optionally selfing selected backcross progeny in order to identify homozygous plants;

(g) crossing at least one of said backcross progeny and/or selfed plants with another inbred cucumber parent plant to generate a hybrid cucumber variety with the desired trait and all of the morphological and physiological characteristics of hybrid cucumber variety when grown in the same environmental conditions.

As indicated, the last backcross generation may be selfed in order to provide for homozygous pure breeding (inbred) progeny exhibiting resistance to *Fusarium*. Thus, the result of recurrent selection, backcrossing and selfing is the generation of lines that are genetically homozygous for the genes associated with *Fusarium*-resistance as well as other genes associated with traits of commercial interest.

It should be noted that heterozygous plants also exhibit *Fusarium*-resistance, and such plants are therefore also an aspect of the present invention.

Cucumber Plants and Seeds

The goal of plant breeding is to combine various desirable traits in a single variety or hybrid. For commercial crops, these traits may include resistance to diseases and insects, tolerance to heat and drought, reducing the time to crop maturity, greater yield, and better agronomic quality. Uniformity of plant characteristics such as germination, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sibling mated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true-bred progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid cucumber variety in a cucumber plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 80% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid cucumber plants can then be generated from this hybrid seed supply.

Using the methods as described above, the skilled person will be able to produce the required inbred lines and from those produce the commercial (F1) hybrid seeds by crossing said inbred lines.

Deposit Information

A deposit of representative seed of each of cucumber lines URS 189 and 05 UR 0327, which are disclosed herein above and referenced in the claims, was made with the NCIMB, located at Ferguson Building, Craibstone Estate, Bucksburn, Aberdeen, AB21 9YA Aberdeen, Scotland. The date of deposit for both accessions was Feb. 18, 2009, and the accession numbers for the deposited seed are NCIMB 41612 and NCIMB 41611, respectively. All restrictions upon the deposit will be irrevocably removed upon the granting of a patent, and the deposit is intended to meet all of the requirements of 37 C.F.R. §1.801-1.809. The deposit will be maintained in the depository for a period of 30 years, or 5 years after the last request, or for the effective life of the patent, whichever is longer, and will be replaced if necessary during that period.

EXAMPLES

*Fusarium* Resistant Plants

Resistance to Forc

Plants of a wide range of cucumber varieties were initially tested for the presence of resistance against *Fusarium oxysporum* f. sp. *radicis cucumerinum* (Forc). This resistance was screened for using a bioassay. Once a potentially resistant accession was identified, multiple independent bioassay experiments were performed on such an accession. The method to determine resistance to *Fusarium* is a "seedling screen". Cucumber seeds are sown in pots filled with 50% peat and 50% sand and incubated in a climate chamber until the cotyledons are fully developed. At this point, the seedlings are removed from the soil and inoculated by dipping the root system in a fungal spore suspension for at least 2 minutes. The concentration of the spores in suspension ranges from $0.4 \times 10^5$ to $4 \times 10^5$ spores/ml, depending on the *Fusarium* strain and season in which the screening is performed. After inoculation, the seedlings are transplanted in moist soil and placed on tables in the greenhouse. Conditions for cultivation include moist soil, which is not wet, a day temperature of 25° C., and artificial light during day time, and preferably a night temperature of at least 17° C. Leaves of susceptible plants wilt 4-14 days post inoculation, dependent on the strain and season. Susceptibility is further demonstrated by cutting the seedling stem from the hypocotyls downward, uncovering brown discoloration of the vascular tissue from top to bottom.

Two accessions were identified that exhibited resistance to Forc. The percentage of resistant plants in these two accessions was recorded at 20 days post inoculation with $4 \times 10^5$ spores per ml. As a susceptible control, the commercial variety Corona was used. This commercial variety is a Long Dutch greenhouse type. Results are depicted in Table 1.

TABLE 1

Accessions URS 189 and MC1278 harbour resistance to Forc.

| Genotype | # of plants tested | Susceptible (#) | Resistant (#) | susceptible (%) | resistant (%) |
|---|---|---|---|---|---|
| URS 189 | 84 | 1 | 83 | 1% | 99% |
| MC1278 | 110 | 43 | 67 | 39% | 61% |
| Corona | 144 | 144 | 0 | 100% | 0% |

The data presented in Table 1 demonstrate that accession MC1278, exhibited intermediate resistance to *Fusarium oxysporum* f. sp. *radicis cucumerinum* (Forc). Accession URS 189 exhibited full resistance to *Fusarium oxysporum* f. sp. *radicis cucumerinum* (Forc).

Resistance to *Fusarium oxysporum* f. sp. *Cucumerinum* and *Fusarium solani* f. sp *cucurbitae*.

Accessions that were identified as harbouring resistance to Forc were then examined for the presence of resistance to *Fusarium oxysporum* f. sp. cucumerinum (Foc)_and *Fusarium solani* f. sp *cucurbitae* (Fsc). Disease progress of Foc was recorded over a period of 17 days post inoculation with $4 \times 10^5$ spores per ml. Disease progress of Fsc was recorded over a period of 14 days post inoculation with $0.4 \times 10^5$ spores per ml. Bioassays were performed in random block design with three repeats of 12 plants each. Again, commercial variety Corona was used as a susceptible control. It was found that URS 189 exhibited resistance to Foc and Fsc.

UR 0327 is used. MC1278 harboured intermediate resistance to Forc. URS 189 is fully resistant to Forc and Foc.

TABLE 2

Accession URS 189 is resistant to Foc and Fsc.

| | Foc | | | Fsc | | |
|---|---|---|---|---|---|---|
| Genotype | average % susceptible | average % resistant | ST. DEV. | average % susceptible | average % resistant | ST. DEV. |
| URS 189 | 0% | 100% | 0 | 0% | 100% | 0 |
| Corona | 100% | 0% | 0 | 100% | 0% | 0 |

Based on Tables 1 and 2, it was concluded that accession URS 189 harbours resistance to Forc, Foc, and Fsc.

Heritability of Resistance to Forc and Foc

Next it was investigated whether introgression of the resistance traits was feasible into progeny plants, and whether stacking of the resistance traits to the two different *Fusarium* isolates could result in further improvement of heritability of resistance.

To this effect, progeny was created from the cross between MC1278 and a susceptible inbred line of a Long Dutch greenhouse type (LDH), and from the cross between URS 189 and LDH. In addition, a cross was prepared between MC1278 and URS 189, and the result of this source-cross was selved for 6 generations to provide a recombinant inbred line (RIL) designated F6 (URS 189×MC1278) or 05 UR 0327. This RIL was subsequently crossed with LDH to reveal the heritability and mechanism of inheritance. Bioassays were performed with Forc in at least two independent experiments of minimum 12 plants each.

First, it was found that the F1 of the cross between MC1278 ×LDH was mostly susceptible to Forc. Of the F1 of the cross between URS 189×LDH almost half of the plants were resistant. Of the F1 of the cross between URS 189×MC1278 two-third of the offspring plants were resistant. Finally, of the F1 of the cross between 05 UR 0327×LDH plants were predominantly resistant (see Table 3). Thus, stacking resistance from URS 189 and MC1278 resulted in a higher level of heritability of resistance in the heterozygous state. The disease incidence decreased.

TABLE 3

Heritability results of Forc resistance in crossing experiments between Forc and/or Foc resistant lines to various isogenic susceptible line.

| Genotype | # of plants tested | Susceptible (#) | Resistant (#) | susceptible (%) | resistant (%) |
|---|---|---|---|---|---|
| F1 (MC1278 × LDH) | 108 | 88 | 20 | 81% | 19% |
| F1 (URS 189 × LDH) | 48 | 26 | 22 | 54% | 46% |
| F1 (URS 189 × MC1278) | 107 | 34 | 73 | 32% | 68% |
| F1 (05 UR 0327 × LDH) | 142 | 26 | 114 | 18% | 82% |

In comparison, Knossos×C566 as described in WO02062130 resulted in an F1 comprising 89% susceptible and 11% resistant plants. Based on the above, it was concluded that combined resistance from URS 189 and MC1278 has a strong additive effect in the heterozygous state. Thus, the plants of the present invention may be heterozygous or homozygous with respect to either of the *Fusarium* resistance introgressions described herein.

Suitable sources of resistance are 05 UR 0327 and URS 189, preferably the combination of the QTLs as present in 05

Coupling Between Forc and Foc Resistance

In a follow-up experiment, it was investigated whether there was a relationship between resistance to Forc and Foc. Recombinant inbred lines (RILs) lines were generated from a single cross of URS 189×MC1278. The F1 was selfed and 300 F2 individuals were propagated until F6 in the absence of selection.

From these RIL 19 plants that exhibited either strong resistance to Forc, or exhibiting strong susceptibility to Forc were selected. Disease progress was recorded over a period of 17 days post inoculation with $4\times10^5$ spores per ml. Bioassays were performed in random block design with three repeats of 12 plants each (36 in total). Corona was used as the susceptible control. It was found that the plants that exhibited strong resistance to Forc also displayed strong resistance to Foc, whereas plants that exhibited strong susceptibility of Forc also exhibited strong susceptibility to Foc. Thus, these plants displayed a similar response to infection with Forc and Foc (see Table 4).

TABLE 4

Results of susceptibility tests for a subset of recombinant inbred lines (RILs) selected on the exclusive basis of strong resistance or susceptibility to Forc.

| RIL F6 (URS 189 × MC1278) no. | Forc | | Foc | |
|---|---|---|---|---|
| | AV. % RESIST | ST DEV | AV. % RESIST | ST DEV |
| 1 | 97 | 5 | 83 | 14 |
| 2 | 97 | 5 | 97 | 5 |
| 3 | 92 | 8 | 92 | 13 |
| 4 | 86 | 17 | 97 | 5 |
| 5 | 83 | 14 | 100 | 0 |
| 6 | 75 | 43 | 91 | 0 |
| 7 | 69 | 21 | 97 | 5 |
| 8 | 67 | 26 | 92 | 14 |
| 9 | 67 | 30 | 47 | 41 |
| 10 | 61 | 34 | 83 | 22 |
| 11 | 58 | 38 | 83 | 8 |
| 12 | 53 | 21 | 94 | 5 |
| 13 | 14 | 13 | 31 | 21 |
| 14 | 3 | 5 | 22 | 21 |
| 15 | 3 | 5 | 33 | 8 |
| 16 | 0 | 0 | 33 | 14 |
| 17 | 0 | 0 | 3 | 5 |
| 18 | 0 | 0 | 0 | 0 |
| 19 | 0 | 0 | 0 | 0 |
| Corona | 0 | 0 | 0 | 0 |

Moreover, multivariate analysis demonstrated that resistance to Forc and Foc was highly correlated in the RIL lines tested (see Table 5).

TABLE 5

Multivariate analysis of RIL lines and their resistance to Forc and Foc.

|  | Forc | Foc |
|---|---|---|
| Forc | 1.0000 | 0.9150 |
| Foc | 0.9150 | 1.0000 |

Figure 1B:
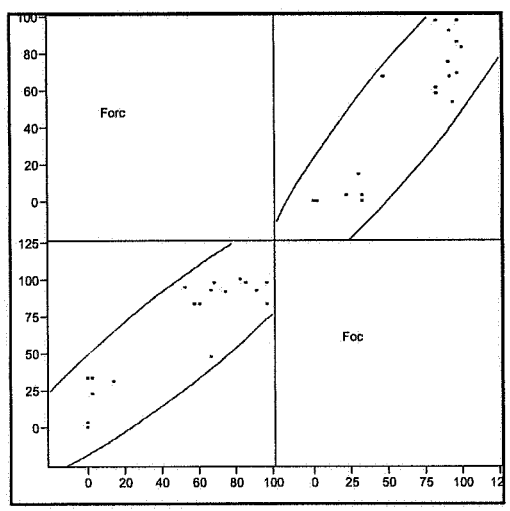
Figure 2:
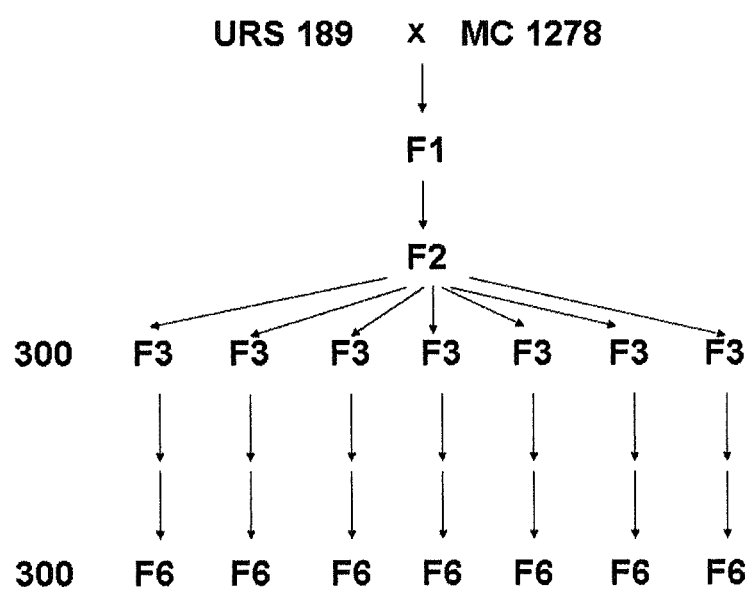
FIG. 2 shows a breeding scheme for the development of a RIL population between two inbred lines harbouring *Fusarium* resistance as described herein. As a mother plant URS 189 and as a father plant MC1278 was used. A reciprocal cross would result in a nearly identical RIL population.

Thus, Forc and Foc resistance co-segregate in strong resistant and susceptible RIL lines. This is further demonstrated in FIG. 1.

Mapping of the Resistance QTLs

A Bulked Segregant Analysis (BSA) was performed on bulks of respectively 47 resistant and 47 susceptible F6 RILs with 15 AFLP primer combinations (PCs). A genetic map was developed on 94 individuals. The map consisted of 161 markers, with 72% genome coverage. Each LG was linked to a public map by multiple anchor markers (Table 6). QTL analysis revealed two QTLs in the resistant RIL lines. The QTLs were validated by screening closely linked markers on 186 RIL individuals, and LOD values and percentage of explained variance were determined. Subsequently, a second BSA was performed to generate additional markers in the QTL1 region, resulting in a recombinant map of the genetic interval on Linkage Group G and/or R. These markers were applied in high density genotyping of homozygous QIR families used for fine-mapping of $QTL1^{MC1278}$.

The results of the quantitative genetic study into Fusarium resistance from URS 189 and MC1278 in a RIL population of 300 F6 lines revealed that $QTL1^{MC1278}$ is positioned on Linkage Group G and/or R, and has a LOD value of 28.43. It explains 34.09% of the variance. Fine-mapping of QTL1 resulted in two closely linked QTL that are both required for resistance. Closely linked markers are any one of SEQ ID NOs 1-4.

It was further revealed that $QTL2^{URS\ 189}$ is positioned on Linkage Group N, and has a LOD value of 3.93. It explains 4.95% of variance between bulked segregants. A closely linked marker is SEQ ID No. 5.

In contrast to Vakalounakis (Vakalounakis, D. J., 1993. Inheritance and genetic linkage of fusarium wilt (Fusarium oxysporum f. sp. cucumerinum race 1) and scab (Cladosporium cucumerinum) resistance genes in cucumber (Cucumis sativus). Annals of Applied Biology 123: 359-365), no evidence was found that resistance to Fusarium was genetically linked to Ccu, a locus conferring resistance to Cladosporium cucumerinum.

TABLE 6

Linkage analysis of the two QTLs found in the RIL lines and derived from Forc- and Foc-resistant URS 189 and MC1278.

| Locus (trait) | Linkage Group (*) | Linked public markers (LG) |
|---|---|---|
| $QTL^{MC1278}$ (resistance to Forc) | G and/or R | RAPDs: AD14.900 (G), AT15.860 (G), BC592.1150 (G), C7.1500 (R), C7.2100 (R), RFLPs: CsC124E1, CsC137/H3, CsC147E1, CsC157E1, CsC362/E1, CsC558/H3 (G), CsC588H3, CsC611D1, |
| $QTL2^{URS\ 189}$ (resistance to Forc) | N | CsP055D1, CsP280/H3, CsP441/E1, CsP483E1(R) RAPDs: AB14.800, AF17.700, BC388.440, BC388.970, BC403.1600, BC592.2100 |

(*): Park et al., Genome 43: 1003-1010 (2000).

The present QTL study resulted in two resistance-conferring loci, each QTL originates from a different source.

Fine-mapping of QTL1 derived from MC1278 resulted in the identification of two closely linked smaller genetic intervals (sub QTLs) contained within the main QTL, designated as QTL1A and QTL1B.

Marker Sequences

Five sequence IDs are provided in Table 7. SEQ IDs 1-4 are associated with QTL1A and QTL1B. SEQ ID 5 is associated with QTL2. (underlined are the

TABLE 7

Sequence IDs associated with QTL1A and QTL1B and associated with QTL2.

| SEQ. ID. No | Sequence (5'-3') | length (bp) | Allele |
|---|---|---|---|
| 1 | AGCAGTGAGGCCGACTCGTGGAT ATGCTTTCGTTTCTACTAGTCAA GTTGGTGGTCTTGCACCTGATCA CCGGAGCTTGCGATTTGTTCGTC AGGTTTGCTTCTTTTCCTTTTGGC TCTCTGTGACAGCAAAAGATTTT TCCAAGCCTATGTGTAG | 188 | P2 |
| 2 | CCTAATTCGATTTGTTTCCACTA NNNNNNNNNNNNNNNNTCTATAC CAGTGTGTCCTGTGTGAAATTGT TATCCGCTAA | 55 | P2 |
| 3 | TATTCCTGGATGTTTGAGTGATG TTCCTAGTCATCAAAGAAACAAA TCTTCTTTTGATGATGTAAGTTGT CTTTATAAGCTTTCTTCAATATAC GCTTGCACATTCACTTTTAGG | 147 | P2 |
| 4 | AGTTTATGGTAGGTCCATGGACA GTTAGAAGTTTCTCATAAAGAGC AATTATCGTTATCATTTCATTTTT GTTATAGTACTGGTCTCATTTCTT TAGTAAGCCTGGCTTGCGTTCTC TTCTAG | 154 | P1 |
| 5 | AAAATGTGGAGCTCGAGGTTTCG GTGCTGGAGGATGTTCCGCCGTC GTGCGCCGTGGGTCTCCGTCTGC AAGGGTGTAGAAGAGCAGCAAA CAGTCG | 129 | P1 |

P1 = marker is derived from URS 189,
P2 = marker is derived from MC1278

The invention claimed is:

1. A plant of a cucumber breeding line comprising an introgression from cucumber inbred line URS 189, a representative sample of seed of which has been deposited with the NCIMB, Aberdeen, Scotland under accession number NCIMB 41612 and depositors reference URS 189, or comprising an introgression from a *Fusarium*-resistant offspring plant of line URS 189, wherein said introgression confers to said plant of said cucumber breeding line resistance to the causal agent of *Fusarium* stem and root rot, *Fusarium oxysporum* f.sp. *radicis cucumerinum* (Forc); wherein said introgression contains a *Fusarium*-resistence QTL from cucumber inbred line URS 189, or a *Fusarium*-resistance-conferring part thereof, wherein said QTL is indicated by the combination of markers for linkage group N as shown in Table 6.

2. The plant according to claim 1, wherein said *Fusarium*-resistant offspring plant is recombinant inbred line (RIL) 05 UR 0327, a representative sample of seed of which has been deposited with the NCIMB, Aberdeen, Scotland under accession number NCIMB 41611 and depositors reference 05 UR 0327.

3. The plant according to claim 1, wherein said plant comprises at least two introgressions from recombinant inbred line (RIL) 05 UR 0327, wherein both of said two introgressions confer resistance to the causal agent of *Fusarium* stem and root rot, *Fusarium oxysporum* f.sp. *radicis cucumerinum* (Forc), and wherein said at least two introgressions are located on separate linkage groups, wherein one of said introgressions contains a *Fusarium*-resistance QTL that is indicated by the combination of markers for linkage group N as shown in Table 6, or a *Fusarium*-resistance-conferring part thereof, and wherein a second of said introgressions contains a *Fusarium*-resistance QTL that is indicated by the combination of markers for linkage group G and/or R as shown in Table 6, or a *Fusarium*-resistance-conferring part thereof.

4. The plant according to claim 1, wherein said plant is a plant of an essentially homozygous pure elite breeding line.

5. The plant according to claim 1, wherein said plant is resistant to the causal agent of *Fusarium* stem and root rot *Fusarium oxysporum* f.sp. *cucumerinum* (Foc), and to *Fusarium solani* f.sp *cucurbitae* (Fsc).

6. A cucumber seed produced by crossing or selfing the cucumber plant of claim 1.

7. A cucumber plant produced by growing the seed of claim 6.

8. The plant according to claim 7, wherein said plant is resistant to Forc, preferably to Forc, Foc or Fsc.

9. A plant part of the plant of claim 8.

10. The plant part according to claim 9, wherein the plant part is a cucumber fruit or seed.

11. A method for producing a hybrid cucumber seed comprising crossing the plant according to claim 1 with another cucumber plant and harvesting the resultant hybrid cucumber seed.

12. The method according to claim 11, wherein said other cucumber plant is a cucumber plant of an essentially homozygous pure elite breeding line different from the cucumber plant according to claim 1.

13. A hybrid cucumber seed produced by the method of claim 11.

14. A hybrid cucumber plant, produced by growing the hybrid cucumber seed of claim 13.

15. Plant according to claim 14, wherein said plant is resistant to Forc, Foc or Fsc.

16. A plant part of the hybrid cucumber plant of claim 14.

17. A method for improving the *Fusarium*-resistance of a plant of a cucumber breeding line comprising introgressing into said plant a genomic segment from cucumber accession URS 189, a representative sample of seed of which has been deposited with the NCIMB, Aberdeen, Scotland under accession number NCIMB 41612 and depositors reference URS 189, or a genomic segment from a *Fusarium*-resistant offspring plant of line URS 189, conferring resistance to *Fusarium*, said method comprising the steps of:
 a) crossing a plant of a cucumber breeding line with a plant of cucumber line URS 189 or with a *Fusarium*-resistant offspring plant thereof;
 b) selecting a progeny cucumber plant resulting from said crossing having an introgression from cucumber accession URS 189 or from said *Fusarium*-resistant offspring plant of line URS 189conferring resistance to *Fusarium*;
 c) selfing said progeny cucumber plant selected in step (b) and/or backcrossing said progeny cucumber plant selected in step (b) using said cucumber breeding line as a recurrent parent;
 d) selecting a progeny cucumber plant resulting from the selfing or backcrossing in step (c) having an introgression from cucumber accession URS 189 or from said *Fusarium*-resistant offspring plant of line URS 189, conferring resistance to *Fusarium*;
 e) repeating said steps of selfing and/or backcrossing and selection of steps (c) and (d), to thereby provide a plant of a cucumber breeding line essentially homozygous for said introgression,
 wherein preferably at least one selection as performed in steps (b) or (d) is performed by marker-assisted selection:
 wherein said introgression contains a *Fusarium*-resistance QTL from cucumber inbred line URS 189, or a *Fusarium*-resistance-conferring part thereof, wherein said QTL is indicated by the combination of markers for linkage group N as shown in Table 6.

18. Method according to claim 17, wherein said *Fusarium*-resistant offspring plant is recombinant inbred line (RIL) 05 UR 0327.

19. Method according to claim 17, wherein said method comprises introgressing into said plant of said breeding line at least two introgressions from recombinant inbred line (RIL) 05 UR 0327, wherein both of said at least two introgressions confer resistance to *Fusarium oxysporum* f.sp. *radicis cucumerinum* (Forc), and wherein said at least two introgressions are located on separate linkage groups, wherein one of said introgressions contains a *Fusarium*-resistance QTL that is indicated by the combination of markers for linkage group N as shown in Table 6, or a *Fusarium*-resistance-conferring part thereof, and wherein a second of said introgressions contains a *Fusarium*-resistance QTL that is indicated by the combination of markers for linkage group G and/or R as shown in Table 6, or a *Fusarium*-resistance-conferring part thereof.

20. A method for improving the *Fusarium*-resistance of an F1cucumber hybrid comprising introgressing into a first parental line of said F1 cucumber hybrid a genomic segment from cucumber accession URS 189, a representative sample of seed of which has been deposited with the NCIMB, Aberdeen, Scotland under accession number NCIMB 41612 and depositors reference URS 189, or from a *Fusarium*-resistant offspring plant of line URS 189, conferring resistance to *Fusarium*, said method comprising the steps of:
 a) crossing a plant of at least a first parental line of said F1 cucumber hybrid with a plant of cucumber line URS 189 or with a *Fusarium*-resistant offspring plant of line URS 189;
 b) selecting a progeny cucumber plant resulting from said crossing having an introgression from cucumber accession URS 189 or from said *Fusarium*-resistant offspring plant of line URS 189conferring resistance to *Fusarium*;
 c) selfing said progeny cucumber plant selected in step (b) and/or backcrossing said progeny cucumber plant using said first parental line of said F1 cucumber hybrid as a recurrent parent;
 d) selecting a progeny cucumber plant resulting from the selfing or backcrossing in step (c) having an introgression from cucumber accession URS 189 or from said progeny plant of line URS 189 conferring resistance to *Fusarium*;
 e) repeating said steps of selfing and/or backcrossing and selection of steps (c) and (d) to provide a first parental line of said F1 cucumber hybrid essentially homozygous for said introgression,
 f) using said first parental line obtained in step (e) as a parental line for the production of an F1hybrid having resistance to *Fusarium*,
 wherein preferably at least one selection as performed in steps (b) or (d) is performed by marker-assisted selection; wherein said introgression contains a *Fusarium*-resistance QTL from cucumber inbred line URS 189, or a *Fusarium*-resistance-conferring part thereof, wherein said QTL is indicated by the combination of markers for linkage group N as shown in Table 6.

21. The method according to claim 20, wherein said method further comprises introgressing into said first parental line or in a second parental line of said F1 cucumber hybrid at least two introgressions from recombinant inbred line (RIL) 05 UR 0327, wherein both of said at least two introgressions confer resistance to *Fusarium oxysporum* f.sp. *radicis cucumerinum* (Forc), and wherein said introgressions are located on separate linkage groups; wherein one of said introgressions contains a *Fusarium*-resistance QTL that is indicated by the combination of markers for linkage group N as shown in Table 6, or a *Fusarium*-resistance-conferring part thereof, and wherein a second of said introgressions contains a *Fusarium*-resistance QTL that is indicated by the combination of markers for linkage group G and/or R as shown in Table 6, or a *Fusarium*-resistance-conferring part thereof.

22. The method according to claim 17, wherein said marker-assisted selection procedure comprises the selection for markers having the sequence of any one of SEQ ID No. 1-5.

23. A *Fusarium*-resistant cucumber breeding line or a *Fusarium*-resistant F1 cucumber hybrid obtained by a method according to claim 17.

24. A method for the detection of a QTL associated with resistance to *Fusarium* in cucumber plants comprising detecting a genetic marker being one or more of SEQ ID Nos 1-5.

25. A method for selecting a cucumber plant or part thereof, including a seed, comprising the steps of:
(a) providing a progeny cucumber plant or part thereof by crossing a plant of a cucumber breeding line with a plant of cucumber line URS 189 or with a *Fusarium*-resistant offspring plant of line URS 189;
(b) testing said progeny cucumber plant or part thereof for the presence of an introgression segment from cucumber accession URS 189 or from a *Fusarium*-resistant offspring plant of line URS 189;
(c) selecting said progeny cucumber plant or part thereof based on the information derived from said test in step (b); and
(d) optionally using said information for further breeding considerations.

* * * * *

UNITED STATES PATENT AND TRADEMARK OFFICE
CERTIFICATE OF CORRECTION

PATENT NO. : 8,841,516 B2  
APPLICATION NO. : 13/203269  
DATED : September 23, 2014  
INVENTOR(S) : Maarten Johan Kulilela de Milliano et al.

Page 1 of 1

It is certified that error appears in the above-identified patent and that said Letters Patent is hereby corrected as shown below:

On the Title Page, Item (30), please delete "09153969" and insert --09153969.2--

In the Claims

Column 27, Line 60, please delete "189conferring" and insert --189 conferring--

Column 28, Line 34, please delete "F1cucumber" and insert --F1 cucumber--

Column 28, Line 49, please delete "189conferring" and insert --189 conferring--

Column 28, Line 64, please delete "F1hybrid" and insert --F1 hybrid--

Signed and Sealed this  
Third Day of February, 2015

Michelle K. Lee  
*Deputy Director of the United States Patent and Trademark Office*

SEQUENCE LISTING

<160> NUMBER OF SEQ ID NOS: 5

<210> SEQ ID NO 1
<211> LENGTH: 156

```
<212> TYPE: DNA
<213> ORGANISM: Cucumis sativus

<400> SEQUENCE: 1
agcagtgagg ccgactcgtg gatatgcttt cgtttctact agtcaagttg gtggtcttgc        60
acctgatcac cggagcttgc gatttgttcg tcaggtttgc ttcttttcct tttggctctc       120
tgtgacagca aaagattttt ccaagcctat gtgtag                                 156

<210> SEQ ID NO 2
<211> LENGTH: 77
<212> TYPE: DNA
<213> ORGANISM: Cucumis sativus
<220> FEATURE:
<221> NAME/KEY: misc_feature
<222> LOCATION: (24)..(37)
<223> OTHER INFORMATION: Wherein "N" is G, A, T or C

<400> SEQUENCE: 2
cctaattcga tttgtttcca ctannnnnnn nnnnnnntct ataccagtgt gtcctgtgtg        60
aaattgttat ccgctaa                                                       77

<210> SEQ ID NO 3
<211> LENGTH: 115
<212> TYPE: DNA
<213> ORGANISM: Cucumis sativus

<400> SEQUENCE: 3
tattcctgga tgtttgagtg atgttcctag tcatcaaaga aacaaatctt cttttgatga        60
tgtaagttgt ctttataagc tttcttcaat atacgcttgc acattcactt ttagg           115

<210> SEQ ID NO 4
<211> LENGTH: 123
<212> TYPE: DNA
<213> ORGANISM: Cucumis sativus

<400> SEQUENCE: 4
agtttatggt aggtccatgg acagttagaa gtttctcata aagagcaatt atcgttatca        60
tttcattttt gttatagtac tggtctcatt tctttagtaa gcctggcttg cgttctcttc       120
tag                                                                     123

<210> SEQ ID NO 5
<211> LENGTH: 97
<212> TYPE: DNA
<213> ORGANISM: Cucumis sativus

<400> SEQUENCE: 5
aaaatgtgga gctcgaggtt tcggtgctgg aggatgttcc gccgtcgtgc gccgtgggtc        60
tccgtctgca agggtgtaga agagcagcaa acagtcg                                 97
```